United States Patent [19]

Sawai et al.

[11] Patent Number: 5,621,003
[45] Date of Patent: Apr. 15, 1997

[54] MAILLARD REACTION INHIBITOR

[75] Inventors: Kiichi Sawai; Takahiko Mitani, both of Nagoya; Naohisa Ninomiya; Yoshiro Ishiwata, both of Aichi, all of Japan

[73] Assignee: Sanwa Kagaku Kenkyusho Co., Ltd., Nagoya, Japan

[21] Appl. No.: 515,330

[22] Filed: Aug. 15, 1995

[30] Foreign Application Priority Data

Aug. 26, 1994 [JP] Japan .................................. 6-201616

[51] Int. Cl.$^6$ ........................................ A61K 31/28
[52] U.S. Cl. ............................................ 514/492
[58] Field of Search .................................... 514/492

[56] References Cited

U.S. PATENT DOCUMENTS

| | | | |
|---|---|---|---|
| 4,889,715 | 12/1989 | Sawai et al. | 424/80 |
| 5,008,416 | 4/1991 | Kurone et al. | 424/650 |
| 5,240,700 | 8/1993 | Sawai et al. | 424/78.37 |
| 5,260,056 | 11/1993 | Sawai et al. | 424/85.4 |
| 5,279,835 | 1/1994 | Sawai et al. | 424/464 |
| 5,336,688 | 8/1994 | Sawai et al. | 514/492 |
| 5,340,806 | 8/1994 | Sawai et al. | 514/184 |

OTHER PUBLICATIONS

Tokuda et al, *Yakuri/Pharmacometrics*, 46(1):39–43 (1993).
The Washington Post (Feb., 1995).
*AIDS*, 8(1):561–569 (1994).
Sternbert, *BioWorld Today*, 6(22):1–5 (1995).

*Primary Examiner*—Raymond Henley, III
*Attorney, Agent, or Firm*—Sughrue, Mion, Zinn, Macpeak & Seas

[57] ABSTRACT

A maillard reaction inhibitor comprising, as the principal component, an eight-structural polymer of 3-oxygermylpropionic acid represented by the following stereostructure (I):

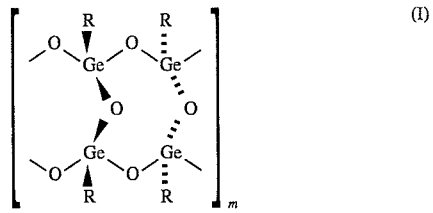

wherein R represents —$CH_2CH_2COOH$, and m is a weight average polymerization degree calculated on the basis of the weight average molecular weight of propagermanium propyl ester and is 137±84 (137 on average with a standard deviation of ±3σ); and having the following minimum constitutional unit:

$(O_{1/2})_3GeCH_2CH_2COOH$ and the following empirical formula:

$C_6H_{10}Ge_2O_7,$ a method for inhibiting the Maillard reaction, and a method for preventing and treating diseases caused by Maillard reaction such as diabetes and concurrent diseases thereof.

2 Claims, 1 Drawing Sheet

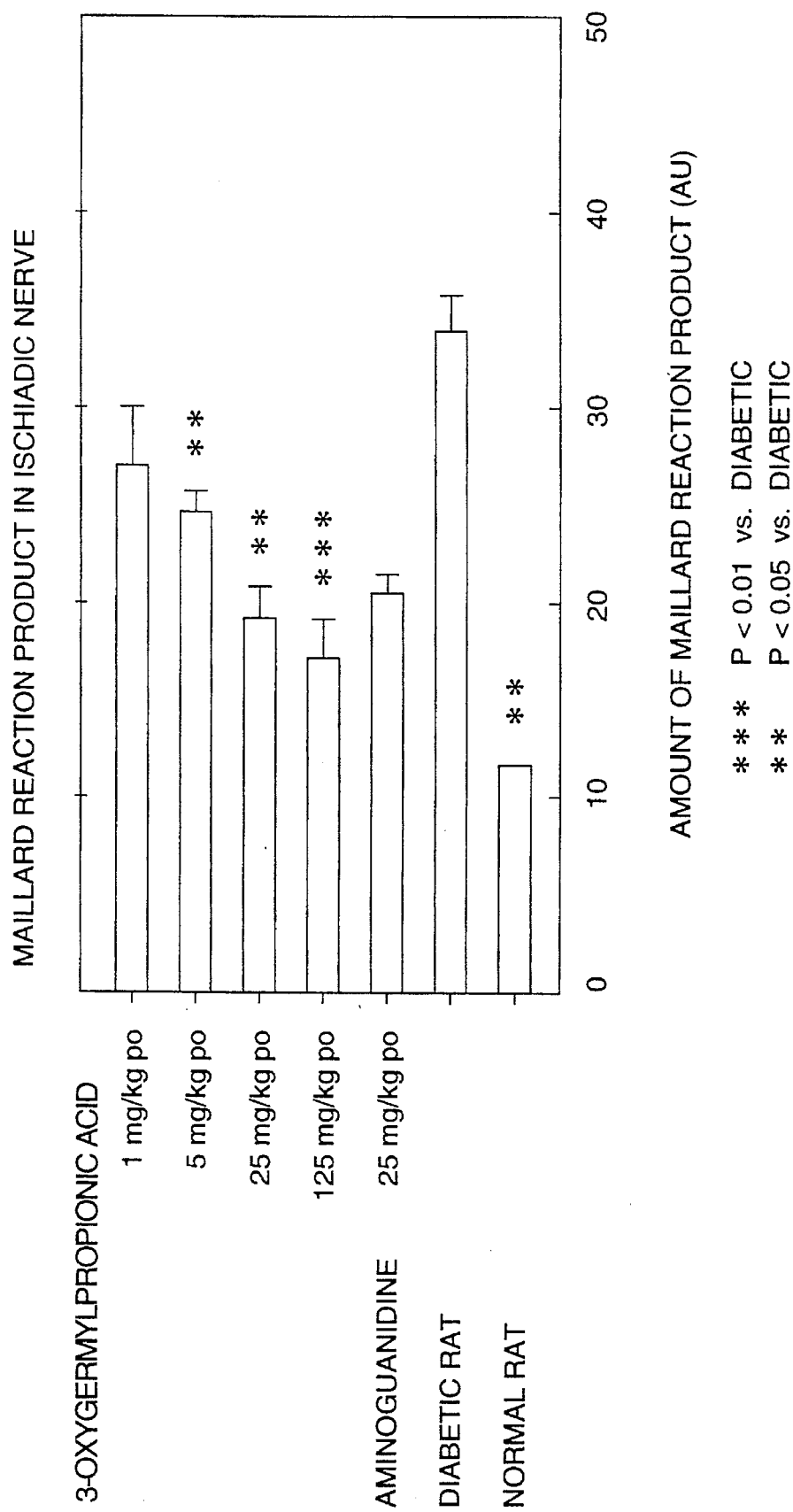

MAILLARD REACTION INHIBITOR

FIELD OF THE INVENTION

This invention relates to a maillard reaction inhibitor comprising, as the principal component, an eight-structural polymer of 3-oxygermylpropionic acid represented by the following stereostructure (I):

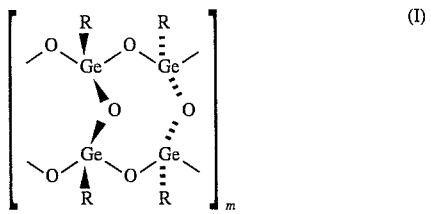

wherein R represents —$CH_2CH_2COOH$, and m is a weight average polymerization degree calculated on the basis of the weight average molecular weight of propagermanium propyl ester and is 137±84 (137 on average with a standard deviation of ±3σ); and having the following minimum constitutional unit:

$(O_{1/2})_3GeCH_2CH_2COOH$ and the following empirical formula:

$C_6H_{10}Ge_2O_7$

The present invention also relates to a method for inhibiting the Maillard reaction and a method for preventing and treating diseases caused by Maillard reaction such as diabetes and concurrent diseases thereof.

The compound preferably is administered as a composition comprising a carrier for stabilizing the pharmacological activity. Preferably the carrier is composed of sugars or modified celluloses, in particular, hydroxypropylcellulose. Preferably the composition contains from 0.005 to 5% by weight of 3-oxygermylpropionic acid and from 0.005 to 50% by weight of the carrier for stabilizing the pharmacological activity.

BACKGROUND OF THE INVENTION

Since 3-oxygermylpropionic acid undergoes polymerization in a complicated manner and is useful for various applications, it has attracted attention of many researchers from the viewpoints of pharmacological activities in recent years. JP-B-63-62492 discloses anti-cataract, as well as other, activities of this compound (The term "JP-B" as used herein means an "examined Japanese patent publication"). Further, it was reported that carboxyethylgermanium sesquioxide, which has been known for a long time and which is generally called Ge132, has a twelve-membered ring structure (*J. Am. Chem. Soc.*, vol. 98(25), pp. 8287 (1976)). However, this compound has some disadvantages. For example, the pharmacological activities thereof vary from lot to lot. In addition, the activities of the compound decrease, for example, due to processing conditions or upon dispensing.

As the maillard reaction inhibitor, the compounds disclosed in JP-B-67827, EP-A-0638075, and the like are known. However, there are demand for new maillard reaction inhibitors which are different from these compounds.

The present inventors have conducted extensive studies on preparation methods whereby the inherent pharmacological activities of 3-oxygermylpropionic acid can be sustained in a stable state. They have further studied the mechanism of action of this compound in vivo. As a result, the inventors discovered various substances that can serve as a stabilizer for 3-oxygermylpropionic acid (JP-A-61-65819 and U.S. Pat. Nos. 4,889,715 and 5,340,806) and the inventors also found that sugars serve to enhance the pharmacological activities thereof (JP-A-60-190714 and U.S. Pat. Nos. 5,336,688 and 5,260,056) (The term "JP-A" as used herein means an "unexamined published Japanese patent application").

The structure of carboxyethylgermanium sesquioxide has already been determined (*J. Am. Chem. Soc.*, vol. 98(25), pp. 8287 (1976)). JP-B-57-53800 suggests the possibility of the existence of various 3-oxygermylpropionic acid compounds. However, these substances each suffers from the above-mentioned problems.

SUMMARY OF THE INVENTION

The present inventors have conducted extensive studies on a number of known compounds including those described in JP-B-57-53800 in order to solve the activities problems of 3-oxygermylpropionic acid, which problems are caused by differences in the synthetic operations and physicochemical procedures. As a result, they have proved the existence of a compound having various stereostructures. Further, the inventors have identified the pharmacological effects thereof depending on the stereostructure. Thus, they have found out that a compound, which has been considered to be represented by $[(O_{1/2})_3GeCH_2CH_2COOH]_n$, has a number of stereostructures (s-type, w-type, and c-type as shown below) and its activity varies depending on the degree of polymerization.

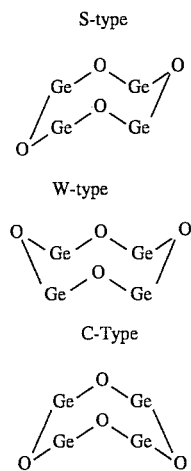

Then, they have specified a structure and a weight average polymerization degree whereby the highest activity can be attained from among these compounds.

BRIEF DESCRIPTION OF THE DRAWINGS

FIG. 1 shows the inhibiting effect of the compound of the present invention on the production of the Maillard reaction product in the collagenous tissue in ischiadic nerve.

DETAILED DESCRIPTION OF THE INVENTION

The chemical and physical properties of the compound according to the present invention are as summarized in Tables 1 and 2 below. In these Tables, the compound of the present invention is referred to as 8-structural SK818.

Table 1 shows the results of the molecular weight measurement by the light scattering method. Table 2 shows the lattice constant determined by the powder X-ray diffraction method. For the measurement of the molecular weight, the polymer of 3-oxygermylpropionic acid was converted to its propyl ester by using diazopropane, and the molecular weight of the propyl ester was measured by the light scattering method (the Zimm plot analysis). Then, the equivalent molecular weight of the polymer of 3-oxygermylpropionic acid was calculated. Table 3 gives the data on the comparison in physical properties with a known germanium compound (12-membered Ge132). The data were obtained by the conventional methods (cf. *Japanese Pharmacopeia* twelfth revision).

TABLE 1

(Weight-average molecular weight of SK-818)

|  | SK-818 propyl ester | SK-818 (equivalent value) |
|---|---|---|
| Weight average molecular weight ($\overline{Mw}$) |  |  |
| Average ($\overline{X}$) | $1.16 \times 10^5$ | $9.29 \times 10^4$ |
| Standard deviation ($3\sigma$) | $\pm 0.71 \times 10^5$ | $\pm 5.72 \times 10^4$ |
| Molecular formula* | $(C_6H_{11}GeO_{3.5})_n$ | $(C_3H_5GeO_{3.5})_n$ |
| Weight average polymerization degree (n)* | $548 \pm 337$ | $137 \pm 84$ |

*n is an integer determined from the constitutional unit, provided that the minimum constitutional unit of SK-818 is $(O_{1/2})_3GeCH_2CH_2COOH$.

TABLE 2

| Chemical formula*[1] | $C_3H_5GeO_{3.5}$ |
|---|---|
| Formula weight*[1] | 169.66 |
| Crystal class | monoclinic |
| Space group | — |
| Unit cell parameters |  |
| a (Å) | 13.35 (1) |
| b (Å) | 5.03 (1) |
| c (Å) | 7.55 (2) |
| $\beta$ (deg.) | 94.3 (2) |
| vol (Å$^3$) | 505.4*[2] |
| z | 4*[3] |
| Density (gcm$^{-1}$) | 2.23*[4] |

*[1]Indication is given provided that the minimum constitutional unit of SK-818 is $(O_{1/2})_3GeCH_2CH_2COOH$.
*[2]Calculated on the basis of the lattice constant.
*[3]Calculated on the basis of the lattice constant and the measured density.
*[4]Measured by the floating method (cf. Shinjikkenkagakukoza, No. 17, pp. 551–552.).

TABLE 3

(Comparison of general physical properties)

| | SK-818 | Ge-132 |
|---|---|---|
| (1) | H = 3.02%, C = 21.10% | H = 3.01%, C = 21.15% |
| (2) | $\lambda_{max}$ = 192.5 nm, $E_{1cm}^{1\%}$ = 3.73 | $\lambda_{max}$ = 192.5 nm, $E_{1cm}^{1\%}$ = 3.75 |
| (3) | 1696 cm$^{-1}$, 1435 cm$^{-1}$, 1255 cm$^{-1}$, 890 cm$^{-1}$, 805 cm$^{-1}$ | 1690 cm$^{-1}$, 1410 cm$^{-1}$, 1240 cm$^{-1}$, 905 cm$^{-1}$, 790 cm$^{-1}$, 730 cm$^{-1}$ |
| (4) | 456 cm$^{-1}$ | 449 cm$^{-1}$ |
| (5) | $2\theta$ = 6.5°, 11.5°, 13.7°, 21.0°, 22.3° | $2\theta$ = 7.8°, 15.5°, 19.2°, 20.6°, 22.0°, 26.0° |
| (6) | ($\delta$ ppm, D$_2$O): 2.69 (2H, t, J = 7.6, Ge—CH$_2$—$\underline{CH_2}$—) 1.61 (2H, t, J = 7.6, Ge—$\underline{CH_2}$—CH$_2$—) | ($\delta$ ppm, D$_2$O): 2.69 (2H, t, J = 7.6, Ge—CH$_2$—$\underline{CH_2}$—) 1.61 (2H, t, J = 7.6, Ge—$\underline{CH_2}$—CH$_2$—) |
| (7) | $\delta$ppm: 181.87 (Ge—CH$_2$—CH$_2$—$\underline{C}$OOH) 28.24, 29.79, 30.86 (Ge—$\underline{C}$H$_2$—CH$_2$—COOH) 16.38, 16.95, 18.41 (Ge—$\underline{C}$H$_2$—CH$_2$—COOH) | $\delta$ppm: 181.30 (Ge—CH$_2$—CH$_2$—$\underline{C}$OOH) 28.43 (Ge—CH$_2$—$\underline{C}$H$_2$—COOH) 15.68 (Ge—$\underline{C}$H$_2$—CH$_2$—COOH) |
| (8) | Peak temp. 252° C. $\Delta$H 48.4 mcal/mg | Peak temp. 189° C., 282° C. $\Delta$H 46.8 mcal/mg |
| (9) | Needles | Amorphous |
| (10) | 1.57% | 1.17% |

(1) Elemental analysis,
(2) UV spectrum,
(3) IR spectrum,
(4) Raman spectrum,
(5) Powder X-ray diffraction,
(6) $^1$H NMR spectrum (liquid),
(7) $^{13}$C NMR spectrum (solid),
(8) DSR,
(9) Crystal form,
(10) Solubility in water determined by the paddle method The eight-structural polymer of 3-oxygermylpropionic acid can be prepared, for example, as follows. That is, one mole portion of 3-trichlorogermylpropionic acid is dissolved in 1 to 2 liters of a non-toxic solvent which dissolves in water (e.g., acetone, acetonitrile, dioxane, and dimethyl formamide), and 1 to 2 liters of water is gradually added to the resulting solution, followed by crystallization. When acetone or the like is used as a solvent, water is added preferably at a temperature of from 0° to 20° C. Then, the resulting crystals are removed by filtration and subjected to drying.

When 3-oxygermylpropionic acid according to the present invention is administered to humans in practice, it is preferably used in the form of an activator composition containing from 0.005 to 5% by weight of the compound of the present invention together with 0.005 to 50% by weight of a carrier for stabilizing the pharmacological activity thereof, and a vehicle. The pharmaceutical composition of the present invention is particularly effective in inhibiting the Maillard reaction and in preventing and treating diseases caused by Maillard reaction such as diabetes and concurrent diseases thereof.

As the carrier for stabilizing the pharmacological activity, sugars (in particular, lactose, sucrose and dextrans), modified celluloses (e.g., hydroxypropylcellulose, carboxymethylcellulose, and hydroxypropylmethylcellulose,, in particular, hydroxypropylcellulose) and naturally occurring polymers (in particular, albumin) may be used. Illustrative examples of the vehicle include hydroxypropylmethylcellulose, polyvinylpyrrolidone, gelatin, lactose, and hydroxypropylcellulose, and those disclosed in U.S. Pat. No. 5,260,056. If desired, the composition may additionally contain a drug which has a high direct therapeutic effect and is generally employed for the aforementioned diseases. Illustrative examples of suitable drugs include antiviral agents for viral hepatitis, antiallergic agents for allergic diseases and anticancerous agents for cancer. By using such a drug in combination with the compound of the present invention, the toxicity of the drug may be relieved while maintaining the curative activities high.

(Administration form and dose)

The 3-oxygermylpropionic acid according to the present invention may be employed in any usual administration form. Depending upon the type of the drug, the pharmaceutical composition may be formulated into an enteral form. The 3-oxygermylpropionic acid of the present invention is generally administered to humans at a dose of 1 to 1,500 mg/day, though the dose may vary depending upon the type or form of the preparation, the age of patients, etc. In the case of adults (weighing 50 kg), for example, the dose is preferably about 150 mg/day.

The following Preparation Examples, Efficacy and Pharmacology Test Examples and Formulation Examples will further illustrate the present invention in greater detail.

PREPARATION EXAMPLE

A 252 g (1 mol) portion of 3-trichlorogermylpropionic acid was dissolved in 2 liters of acetone. Then, 1.5 l of water was added to the resulting solution and the resulting mixture was allowed to stand several hours while maintaining the temperature at 10° to 20° C. After allowing the resulting mixture to stand day and night, the crystals thus precipitated were filtered under suction, washed with acetone and dried under reduced pressure. Thus, 3-oxygermylpropionic acid polymer was obtained with a yield of 90%.

A minimum constitutional unit: $(O_{1/2})_3GeCH_2CH_2COOH$

An empirical formula: $C_6H_{10}Ge_2O_7$, m.p.: about 230° C. (decomp.)

Property: white crystalline powders with no smell and a slight sourness. Hardly soluble in water and scarcely soluble in ethanol, acetone, ether, dichloromethane and hexane The molecular weight and the lattice constant of the compound of the present invention thus obtained were determined respectively by the light scattering method and the powder X-ray diffraction method. Tables 1 and 2 show the results.

PREPARATION OF COMPOSITION EXAMPLE

With the use of ethanol (90 g) as a wetting agent, 2 parts of the compound of the present invention (200 g) and 1 part of hydroxypropylcellulose (100 g) were kneaded together. The kneaded blend was then dried at 50° C. or below to thereby obtain a powdery or granular composition.

PREPARATION OF PHARMACEUTICAL COMPOSITION EXAMPLE

Tablets:

Compressed tablets were prepared in accordance with the following formulation.

| | |
|---|---|
| 3-Oxygermylpropionic acid polymer | 10.0 |
| Lactose | 159.2 |
| Carboxymethylcellulose Na (CMC—Na) | 9.0 |
| Light anhydrous silicic acid | 2.0 |
| Magnesium stearate | 1.8 |
| | 180.0 mg |

EFFICACY AND PHARMACOLOGY TEST EXAMPLE 1

(Comparison in usefulness between the compound of the present invention and a known compound)

a) Purpose

To compare the effect of the compound of the present invention on the antibody production of tumor bearing mice with that of the known compound carboxygermanium sesquioxide (Ge132).

b) Procedure

BALB/c mice aged 7 weeks were each subcutaneously implanted with $2 \times 10^6$ Sarcoma-180 cells. Nine days after the transplantation, the compound of the present invention or Ge132 was daily administered to the mice at doses of 0.3, 1, 3, 10 and 30 mg/kg/day consecutively for 5 days. On the next day of the final administration, each mouse was sensitized by intravenously injecting $2 \times 10^8$ sheep red blood cells (SRBC). Four days after the sensitization, the spleen of each animal was collected to measure the amount of anti-SRBC IgM-PFC in the spleen cells.

c) Results and Discussion

Table 4 shows the results of the test on the effects of the compound of the present invention and Ge132 on the antibody production. As seen from Table 4, significant effect was observed at doses of 0.3 to 30 mg/kg of the compound of the present invention. The number of PFC reaches the maximum level at doses between 1 to 3 mg/kg.

In contrast, with Ge132, a significant effect was observed only when the dosage is 30 mg/kg.

Thus, it is appreciated that the compound of the present invention is effective in increasing the antibody producing ability of the tumor-bearing mice and its usefulness is about 100 times as high as that of Ge132.

Table 5 shows the results. As indicated in Table 5, 3-oxygermylpropionic acid of the present invention exhibits an intense effect, i.e., being comparable to that of 5 mM aminoguanidine, of inhibiting Maillard reaction.

TABLE 5

(Inhibitory effect on Maillard reaction between protein and sugar)

| | | Inhibitory ratio (%) | | |
|---|---|---|---|---|
| | | After 7 days | After 14 days | After 28 days |
| BSA-glucose | 3-oxygermylpropionic acid | 72.5 | 67.8 | 61.9 |
| | aminoguanidine | 75.1 | 71.1 | 63.5 |
| BSA-fructose | 3-oxygermylpropionic acid | 80.4 | 75.5 | 72.8 |
| | aminoguanidine | 76.3 | 70.8 | 66.9 |
| LYZ-glucose | 3-oxygermylpropionic acid | 72.3 | 59.4 | 48.6 |
| | aminoguanidine | 76.7 | 63.4 | 53.2 |
| LYZ-fructose | 3-oxygermylpropionic acid | 82.1 | 64.4 | 24.9 |
| | aminoguanidine | 76.0 | 59.2 | 22.4 |

TABLE 4

(Effects of the invention compound and Ge132 on antibody-producing activity of tumor-bearing mice)

| | | IgM-PFC/ $10^6$ spleen cells |
|---|---|---|
| Normal mice group | | 1613 ± 107*** |
| Cancer mice group | | 740 ± 40 |
| Invention compound | 0.3 mg/kg | 984 ± 61** |
| | 1 | 1269 ± 112*** |
| | 3 | 1258 ± 82*** |
| | 10 | 1004 ± 102* |
| | 30 | 909 ± 64* |
| Ge132 | 0.3 mg/kg | 770 ± 77 |
| | 3 | 779 ± 63 |
| | 10 | 805 ± 60 |
| | 30 | 995 ± 69** |

IgM-PFC count is an average in 7 mice ± standard deviation.
Significant difference from the cancer mice group:
*$p < 0.05$,
**$p < 0.01$,
***$p < 0.001$.

EFFICACY AND PHARMACOLOGY TEST EXAMPLE 2

(Maillard reaction-inhibiting effect)

Inhibitory effect of 3-oxygermylpropionic acid according to the present invention on Maillard reaction between protein and sugar:

Bovine serum albumin (BSA) or lysozyme (LYZ), i.e. a protein, was dissolved in a 0.5M phosphate buffer solution (pH 7.4) at 10 mg/ml. Further, glucose or fructose was added to the resulting solution so as to give a final concentration of 400 mM. To the solution thus obtained, 3-oxygermylpropionic acid was added to give a concentration of 100 μg/ml. As a comparative, aminoguanidine of a final concentration of 5 mM was employed. The mixture was incubated in the dark at 37° C. and the amount of a fluorescent substance in the reaction product was measured after a definite period. The excitation wavelength was set to 350 nm while the measurement wavelength was set to 435 nm (in the case of glucose) or 428 nm (in the case of fructose). As a standard, quinine/0.1 $NH_2SO_4$ was used.

EFFICACY AND PHARMACOLOGY TEST EXAMPLE 3

(Maillard reaction-inhibiting effect)

Inhibitory effect of 3-oxygermylpropionic acid according to the present invention on tissue Maillard reaction in streptothricin (ST)-induced diabetic rats:

To SD rats weighing about 200 g, ST was intravenously injected at a dose of 50 mg/kg to thereby induce the onset of diabetes. Then 3-oxygermylpropionic acid according to the present invention was orally administered to the animals at doses of 1, 5, 25 and 125 mg/kg consecutively. As a positive comparative, aminoguanidine was orally administered at a dose of 25 mg/kg consecutively. After 24 weeks, the amounts of the Maillard reaction product in the collagenous tissues in the ischiadic nerve, the retina, the abdominal aorta and the renal cortex were measured by the collagenase digestion method [Monnier V.M. et al., *Proc. Natl. Acad. Sci. USA*, 81, 583 (1984)].

As a result, it is found out that 3-oxygermylpropionic acid of the present invention suppresses the production of the Maillard reaction product in each collagen tissue and, in particular, exhibits significant effects at doses of 5, 25 and 125 mg/kg. Also, the consecutive administration of 25 mg/kg of aminoguanidine shows a significant suppressing effect. FIG. 1 shows the results of the measurement of the Maillard reaction product in the ischiadic nerve.

The present invention provides a pharmaceutical composition comprising an eight-structural organic germanium compound, which has a minimum constitutional unit of $(O_{1/2})_3GeCH_2CH_2COOH$ and an empirical formula of $C_6H_{10}Ge_7OT$, as the major ingredient. As the results of pharmacological tests, it was found out that this compound is useful in inhibiting Maillard reaction and preventing and treating diseases caused by Maillard reaction such as diabetes and concurrent diseases thereof.

While the invention has been described in detail and with reference to specific examples thereof, it will be apparent to one skilled in the art that various changes and modifications can be made therein without departing from the spirit and scope thereof.

What is claimed is:

1. A method for inhibiting the Haillard reaction, other than when treating diabetes, comprising administering an effective amount of an eight-structural polymer of 3-oxygermylpropionic acid represented by the following stereostructure (I):

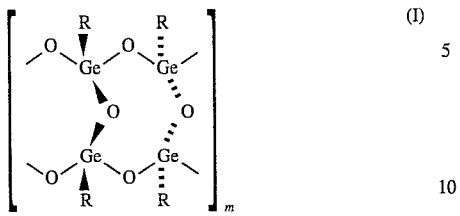

wherein R represents —$CH_2CH_2COOH$, and m is a weight average polymerization degree calculated on the basis of the weight average molecular weight of propagermanium propyl ester and is 137±84, 137 on average with a standard deviation of ±3σ; and having the following minimum constitutional unit:

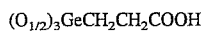

and the following empirical formula:

2. A method for treating a disease caused by the Maillard reaction., wherein said disease is a disease other than diabetes comprising administering an effective amount of an eight-structural polymer of 3-oxygermylpropionic acid represented by the following stereostructure (I):

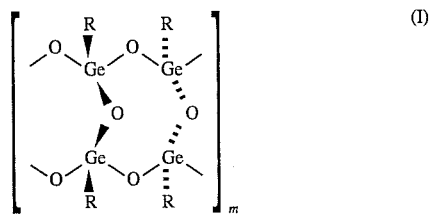

wherein R represents —$CH_2CH_2COOH$, and m is a weight average polymerization degree calculated on the basis of the weight average molecular weight of propagermanium propyl ester and is 137 ±84, 137 on average with a standard deviation of ±3σ; and having the following minimum constitutional unit:

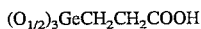

and the following empirical formula:

* * * * *